United States Patent
Morinaka et al.

(10) Patent No.: US 7,417,163 B2
(45) Date of Patent: Aug. 26, 2008

(54) PROCESS FOR PREPARING HIGH PURITY (METH) ACRYLOYLOXYALKYL ISOCYANATE

(75) Inventors: Katsutoshi Morinaka, Fukushima (JP); Kazuyoshi Hoshi, Fukushima (JP)

(73) Assignee: Showa Denko K.K., Tokyo (JP)

( * ) Notice: Subject to any disclaimer, the term of this patent is extended or adjusted under 35 U.S.C. 154(b) by 183 days.

(21) Appl. No.: 10/566,178

(22) PCT Filed: Jul. 27, 2004

(86) PCT No.: PCT/JP2004/011019

§ 371 (c)(1),
(2), (4) Date: Jan. 27, 2006

(87) PCT Pub. No.: WO2005/012237

PCT Pub. Date: Feb. 10, 2005

(65) Prior Publication Data

US 2006/0241319 A1    Oct. 26, 2006

Related U.S. Application Data

(60) Provisional application No. 60/493,455, filed on Aug. 8, 2003.

(30) Foreign Application Priority Data

Jul. 31, 2003    (JP) .............................. 2003-283695

(51) Int. Cl.
*C07C 263/18* (2006.01)
(52) U.S. Cl. ..................................... 560/353
(58) Field of Classification Search .................. 560/352
See application file for complete search history.

(56) References Cited

U.S. PATENT DOCUMENTS 2,821,544 A    1/1958    Holtschmidt
4,278,809 A    7/1981    Burdett
4,310,688 A    1/1982    Mendoza
6,245,935 B1 *  6/2001    Misu et al. .................. 560/218

FOREIGN PATENT DOCUMENTS

| DE | 3225247 A | 1/1984 |
|---|---|---|
| EP | 0936214 A2 | 8/1999 |
| JP | 54-5921 A | 1/1979 |
| JP | 9-32368 A | 12/1997 |
| JP | 9-323958 A | 12/1997 |
| JP | 11-228523 A | 8/1999 |
| JP | 11228523 A * | 8/1999 |

OTHER PUBLICATIONS

Database WPI, Section Ch, Week 199809, Derwent Publications Ltd., London, GB; AN 1998-095671, XP002308557 & JP 09 323968 A (Showa Denko KK), Dec. 16, 1997, abstract.
Database WPI, Section Ch, Week 199315, Derwent Publications Ltd., London, GB; AN 1993-121339, XP002308558 & JP 05 058982 A (Showa Denko KK) Mar. 9, 1993, abstract.
Database WPI, Section Ch, Week 198912, Derwent Publications Ltd., London, GB; AN 1989-090838, XP002308559 & JP 01 042463 A (Showa Rhodia Kagaku), Feb. 14, 1989, abstract.

* cited by examiner

*Primary Examiner*—Paul A Zucker
(74) *Attorney, Agent, or Firm*—Sughrue Mion, PLLC

(57) ABSTRACT

A process for preparing a high purity (meth)acryloyloxyalkyl isocyanate having a very small hydrolyzable chlorine content is provided. The high purity (meth)acryloyloxyalkyl isocyanate is prepared by subjecting a hydrolyzable chlorine containing (meth)acryloyloxyalkyl isocyanate to mixing treatment with an epoxy compound and an amine at a temperature of from 110 to 160° C. to prepare a mixture; and preparing a high purity (meth)acryloyloxyalkyl isocyanate from the resulting mixture with distillation. In particular, it is possible to effectively prevent (meth)acryloyloxyalkyl isocyanate from polymerization during the distillation by adding a polymerization inhibitor such as phenothiazine and the like.

10 Claims, No Drawings

PROCESS FOR PREPARING HIGH PURITY (METH) ACRYLOYLOXYALKYL ISOCYANATE

CROSS REFERENCES OF RELATED APPLICATION

This application is a 371 of PCT//JP04/11019 filed Jul. 27, 2004 which claims benefit of 60/493,455 filed Aug. 8, 2003.

TECHNICAL FIELD

The present invention relates to a process for preparing a high purity (meth)acryloyloxyalkyl isocyanate having a small hydrolyzable chlorine content. In the present specification, "(meth)acryloyl" means acryloyl or methacryloyl. Further, "(meth)acryloyloxyalkyl isocyanate" means a composition substantially consisting of (meth)acryloyloxyalkyl isocyanate capable of containing a slight amount of hydrolyzable chlorine, except for the particular comment on it as a compound.

BACKGROUND ART (Meth)acryloyloxyalkyl isocyanates typified by methacryloyloxyethyl isocyanate are industrially very useful compounds containing, per molecule, an isocyanate group having high reactivity with a compound having an active hydrogen, such as compounds having a substituent e.g. a hydroxyl group, or primary or secondary amino group, and a carbon-carbon double bond capable of vinyl polymerization. They are used in various purposes, for example, paints and coating materials, adhesives, photo-resists, dental materials and magnetic recording materials.

As described in U.S. Pat. No. 2,821,544 and JP-A-S54 (1979)-5921, these compounds are prepared by using phosgene and generally contain impurities called as hydrolyzable chlorine.

When urethane acrylate and the like are prepared using a (meth)acryloyloxyalkyl isocyanate containing hydrolyzable chlorine, the hydrolyzable chlorine works as a catalyst poison and also a chlorine compound contaminated in a product affects the weathering resistance and corrosion resistance of the resulting product. Particularly, when the (meth)acryloyloxyalkyl isocyanate containing hydrolyzable chlorine is used to photo-resist materials for electronic apparatus parts, the presence of hydrolyzable chlorine may induce a serious problem.

Conventionally, various methods of decreasing the amount of hydrolyzable chlorine in an isocyanate compound are proposed.

There are known methods, for example, a method of mixing a hydrolyzable chlorine containing isocyanate compound with a minute alkali metal carbonate at a high temperature for a long period of time, a method of adding a zinc carboxylate and a hindered phenol oxidizing agent to a hydrolyzable chlorine containing isocyanate compound, subjecting to heat treatment, followed by distillation, a method of synthesizing an isocyanate in a solvent insoluble in water, and washing with a sodium hydrogen carbonate aqueous solution, and a method of treating a hydrolyzable chlorine containing polymethylene polyphenyl isocyanate with an epoxy compound. Furthermore, as a method without using a drug such as alkali metal carbonate and the like, there is a method of vaporizing a hydrolyzable chlorine containing isocyanate compound and condensing at a temperature of not lower than 70° C.

These methods, however, cannot decrease the amount of hydrolyzable chlorine sufficiently, or have various problems for solving in order to carry out them industrially. For example, in the method of mixing a hydrolyzable chlorine containing isocyanate compound with a minute alkali metal carbonate at a high temperature, it is difficult to separate the isocyanate compound and the carbonate after the treatment so that the occurrence of loss cannot be avoided. In the method of washing with a sodium hydrogen carbonate aqueous solution, white insoluble matters are deposited on the boundaries between an organic phase and a water phase and the matters cause obstacles in the subsequent separation procedure, or apparatus pollution. In the method of using the sodium salt, the isocyanate compound is liable to be contaminated by sodium ion, and even if the sodium ion content is in the level of ppm, it causes a serious problem in the case of using the isocyanate compound to electronic materials.

In particular, when an isocyanate compound having a carbon-carbon double bond is purified, it is desired to prevent the isocyanate compounds from polymerization reaction and simultaneously to decrease the content of hydrolyzable chlorine effectively. However, the above method cannot lead to the satisfactory results.

U.S. Pat. No. 4,310,688 discloses that a methylene chloride solution of methacryloyloxyethyl isocyanate containing 0.21% of hydrolyzable chlorine is treated with a compound containing a vicinal epoxy group (example: 1,2-butylene oxide) to decrease the hydrolyzable chlorine content to 0.05% by mass. However, this method can decrease the hydrolyzable chlorine content to several hundred ppm at the most, and the purified isocyanate compound prepared by this method is insufficient for the use including electronic materials and the like.

In order to solve the above problems associated with the prior arts, a method of treating with an epoxy compound in the presence of an amine is disclosed as a method of decreasing the hydrolyzable chlorine content in the isocyanate compound (JP-A-H9(1997)-323968. This method is an excellent method, but it cannot remove hydrolyzable chlorine completely. Therefore, the advent of a method of further decreasing the hydrolyzable chlorine content has been desired.

JP-A-H11(1999)-228523 discloses a method of preparing a (meth)acryloyloxyalkyl isocyanate substantially free from hydrolyzable chlorine by adding an amine and an epoxy group containing compound, heating and then purifying with distillation to prepare a purified acryoyloxyalkyl isocyanate substantially free from 2-chloro propionic acid isocyanate alkyl ester, or to prepare a purified methacryloyloxyalkyl isocyanate substantially free from 2-methyl-2-chloropropionic acid isocyanate alkyl ester. This method, however, has many problems in industrialization thereof such that in the case of carrying out distillation once after the addition of an amine and an epoxy group-containing compound, one having a hydrolyzable chlorine content of only 29 ppm is prepared and further, in order to further decrease the hydrolyzable chlorine content, it is necessary to conduct precision distillation.

Meanwhile, a method of preparing an isocyanate compound without using phosgene has been studied. With regard to (meth)acryloyloxyalkyl isocyanates, a method of pyrolysis of an urethane compound is proposed. The process comprises the step of pyrolysis at a high temperature, but the yield is not satisfactory economically because the (meth)acryloyloxyalkyl isocyanate is very easily polymerizable. Furthermore, a method of preparing an isocyanate compound at a relatively lower temperature by making an urethane compound into a dealkoxy silane with silanization is proposed, but in this method, an expensive compound is necessary and unnecessary wastes are produced. Further, this method has no description on the yield, so that it has many economic problems in industrialization.

DISCLOSURE OF INVENTION

The present invention is intended to solve the problems associated with the prior art as described above. It is an object of the invention to provide a process for preparing a high purity (meth)acryloyloxyalkyl isocyanate containing a very slight amount of hydrolyzable chlorine.

The summary of the present invention is as follows.

[1] The process for preparing a high purity (meth)acryloyloxyalkyl isocyanate according to the present invention comprises:

subjecting a hydrolyzable chlorine containing (meth)acryloyloxyalkyl isocyanate to mixing treatment with an epoxy compound and an amine at a temperature of from 110 to 160° C. to prepare a mixture; and preparing a high purity (meth)acryloyloxyalkyl isocyanate from the resulting mixture.

[2] The process for preparing a high purity (meth)acryloyloxyalkyl isocyanate as described in [1] further comprises distilling the resulting mixture to isolate a (meth)acryloyloxyalkyl isocyanate, after the mixing treatment.

[3] The process for preparing a high purity (meth)acryloyloxyalkyl isocyanate as described in [1] or [2] is characterized in that the mixing treatment is carried out by adding a polymerization inhibitor.

[4] The process for preparing a high purity (meth)acryloyloxyalkyl isocyanate as described in [3] further comprises carrying out distillation with adding a polymerization inhibitor after the mixing treatment.

[5] The process for preparing a high purity (meth)acryloyloxyalkyl isocyanate as described in [3] or [4] is characterized in that the polymerization inhibitor is phenothiazine.

[6] The process for preparing a high purity (meth)acryloyloxyalkyl isocyanate as described in [5] is characterized in that the mixing treatment is carried out with adding phenothiazine in an amount of from 0.1 to 20% by mass based on the raw material (meth)acryloyloxyalkyl isocyanate and then the distillation is carried out with adding phenothiazine in an amount of from 3 to 30% by mass based on the raw material (meth)acryloyloxyalkyl isocyanate.

[7] The process for preparing a high purity (meth)acryloyloxyalkyl isocyanate as described in [5] or [6] is characterized in that the total amount of phenothiazine added is from 5 to 50% by mass based on the raw material (meth)acryloyloxy alkyl isocyanate.

[8] The process for preparing a high purity (meth)acryloyloxyalkyl isocyanate as described in any one of [2] to [7] is characterized in that the distillation is carried out at a temperature of not higher than 120° C.

[9] The process for preparing a high purity (meth)acryloyloxyalkyl isocyanate as described in any one of [1] to [8] is characterized in that the amine is at least one selected from 2-alkyl-4-alkyl imidazole (provided that each alkyl group independently has a carbon number of 1 to 3), trialkyl amine (provided that each alkyl group independently has a carbon number of 4 to 15) and a compound represented by the following formula [A]:

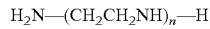    [A]

wherein n is an integer of 2 or more.

[10] The process for preparing a high purity (meth)acryloyloxyalkyl isocyanate as described in [8] is characterized in that the amine is 2-ethyl-4-methylimidazole.

[11] The process for preparing a high purity (meth)acryloyloxyalkyl isocyanate as described in any one of [1] to [10] is characterized in that the (meth)acryloyloxyalkyl isocyanate is (meth)acryoyloxyethyl isocyanate.

The preparation process of the present invention can provide a high purity (meth)acryloyloxyalkyl isocyanate containing a very slight amount of hydrolyzable chlorine, more specifically it provides a high purity (meth)acryloyloxyalkyl isocyanate having a hydrolyzable chlorine content of not more than 10 ppm by distillation once from a (meth)acryloyloxyalkyl isocyanate having a hydrolyzable chlorine content of several hundred ppm.

The addition of the polymerization inhibitor such as phenothiazine and the like can effectively prevent (meth)acryloyloxyalkyl isocyanate from polymerization particularly in the distillation.

BEST MODE FOR CARRYING OUT THE INVENTION

The present invention will be described in detail hereinafter.

The (meth)acryloyloxyalkyl isocyanate submitted to high purification by the preparation process of the present invention is a compound represented by the following formula (I).

In the formula (I), $R^1$ is hydrogen or a methyl group and $R^2$ is an alkylene group, preferably an alkylene group of 2 to 6 carbon atoms.

The process of the invention is preferably applied to high purification for a (meth)acryloyloxyethyl isocyanate of the formula (I) wherein $R^2$ is an ethylene group, particularly methacryloyloxyethyl isocyanate. Among the compounds of the formula (I), (meth)acryloyloxyethyl isocyanate has high reactivity and easy handling, and is easily available.

In the process of the present invention, for example, a (meth)acryloyloxyalkyl isocyanate prepared by using phosgene, as a raw material before purification, has a hydrolyzable chlorine content, which is not particularly limited, of preferably not more than 700 ppm from the viewpoint of economic properties in process, particularly preferably not more than 200 ppm. When the hydrolyzable chlorine content in the raw material is large, it is desired to previously reduce the hydrolyzable chlorine content by employing a method appropriately selected, in accordance with the condition, from a method of distilling under reduced pressure by adding an epoxy group-containing compound (hereinafter referred to as epoxy compound), a method of adding an epoxy compound and amine, treating with heat and distilling under reduced pressure, a method of refluxing with blowing an inert gas such as nitrogen and the like, a method of adding a tertiary amine such as triethyl amine and the like and separating a resulting hydrochloride crystal with filtration, and other methods.

In the present specification, the amount of hydrolyzable chlorine is a value of chlorine determined by a analysis method described in Article 5.7, JIS K 1556 (tolylene diisocyanate testing method) or an analysis method equal to the above method in principal.

In Examples described later, the content of hydrolyzable chlorine was analyzed by introducing 35 ml of methyl alcohol, 15 ml of water and 5 g of a specimen into a 100 ml volume Erlenmeyer flask, fixing a reflux condenser to the flask and refluxing with heat for 30 min, thereafter cooling to room temperature and conducting potentiometric titration by the use of a N/100 silver nitrate solution.

The chlorine compound containing hydrolyzable chlorine (in which hydrolyzable chlorine is bonded) determined the above method is presumed to be not a specific compound but a chlorine compound of plural kinds. It is considered that chlorine in a mixture state composed of plural kinds of chlorine compounds. Specifically, in the case of representing isocyanate alkyl(meth)acrylate by R—NCO, it is considered that examples thereof may include compounds represented by R—NH—COCl, R—NCl$_2$, R—N=C(Cl)—R'.HCl (R' is a vinyl group or isopropenyl group), but the details thereof are unclear.

Furthermore, in the hydrolyzable chlorines bonded to these compounds, ones relatively easily removable and ones difficultly removable are mingled. This mingle thereof is an obstacle to purify (meth)acryloyloxyalkyl isocyanate until the (meth)acryloyloxyalkyl isocyanate substantially contains no hydrolyzable chlorine. However, according to the present invention, it is possible to remove these chlorine compounds simply and sufficiently even under such a condition that various chlorine compounds are mingled.

In the present invention, the (meth)acryloyloxyalkyl isocyanate as described above is subjected to mixing treatment with an epoxy compound and an amine at a temperature of from 110 to 160° C.

As the epoxy compound used in the mixing treatment step, epoxy compounds having a relatively larger difference on boiling point with (meth)acryloyloxyalkyl isocyanate which will be purified is preferably used from the viewpoint of subsequent isolation with distillation. The difference on boiling point is preferably not lower than 5° C., more preferably not lower than 20° C.

Examples of the epoxy compound are not particularly limited as long as it has an epoxy group in its molecule and has no active hydrogen capable of reacting with an isocyanate group, and may include an aliphatic alkylene oxide, alicyclic alkylene oxide, epoxidated aliphatic ester and epoxidated triglyceride.

Examples of the aliphatic alkylene oxide may include propylene oxide, butylene oxide and hexene oxide.

Examples of the alicyclic alkylene oxide may include cyclohexene oxide, cyclopentene oxide and compounds obtainable by linking a substituent to these oxides.

The epoxidated aliphatic acid ester used herein has a molecular weight of about from 300 to 500, and may include an epoxidated alkyl stearate etc.

The epoxidated triglyceride may include those obtainable by oxidizing oils and fats such as soybean oil, cotton-seed oil and the like with hydrogen peroxide in the presence of an acidic catalyst in a solvent such as acetic acid, formic acid, etc, and having a molecular weight of about from 500 to 1500, an iodine value of from 2 to 14 and an oxirane oxygen content of about from 2 to 15%.

The oxirane oxygen content in the epoxy compound is determined by allowing the epoxy compound to react with a known amount of hydrogen chloride, thereafter titrating excess hydrogen chloride with an alkali standard liquid and comparing the titration value with a blank value.

These epoxy compounds may be used singly or in combination with two or more. Of the above described epoxy compounds, it is preferred to use epoxidated fatty acid ester and epoxidated triglyceride.

The epoxy compound is used in an amount of usually from 1 to 5 equivalent, preferably 1.5 to 3 equivalent based on 1 equivalent of hydrolyzable chlorine (1 mol of chlorine atom). When the amount of the epoxy compound is less than 1 equivalent based on 1 equivalent of hydrolyzable chlorine, it is liable to not remove hydrolyzable chlorine sufficiently. From the viewpoint of obtaining the effect of the present invention, the amount is unnecessary to be over 5 equivalent. The equivalent number of the epoxy compound is determined by (number of oxygen atom [oxirane oxygen] constituting the epoxy group contained in the epoxy compound)×(mole number of the epoxy compound).

The amine used in the mixing treatment step may be any one of primary, secondary and tertiary amines and further may be in any one of chain-like, branched and cyclic states. The number of the amino group may be one or plural.

Examples of the amine may include triethylene tetramine, trihepthyl amine, trioctyl amine, trinonyl amine, tridecyl amine, 1,4-diazabicyclo[2.2.2]octane, imidazole, 2-ethyl-4-methyl imidazole, 2,4-dimethyl imidazole, 2-methyl imidazole, 2,4-diethyl imidazole, 1-benzyl-2-methyl imidazole, etc. Preferable examples thereof are 2-alkyl-4-alkyl imidazole (provided that the carbon number of each alkyl group is from 1 to 3), trialkyl amine (provided that the carbon number of each alkyl group is from 4 to 15) and a compound represented by the following formula [A]:

$$H_2N—(CH_2CH_2NH)_n—H \qquad [A]$$

in the formula [A], n is an integer of 2 or more. When n is too greater, it is difficult to regulate the mole number of nitrogen atom to chlorine components. Therefore, n is preferably 2 to 6. More preferable examples thereof are triethylene tetramine, trioctyl amine and 2-ethyl-4-methyl imidazole. These amines can be used singly or in combination with two or more.

These amines are used in an amount of usually from 2 to 20 equivalent, preferably 4 to 10 equivalent based on 1 equivalent of hydrolyzable chlorine (1 mol of chlorine atom). When the amount of the amines is less than 2 equivalent based on 1 equivalent of hydrolyzable chlorine, the resulting effect is not sufficient, meanwhile, when the amount is over 20 equivalent, (meth)acryloyloxyalkyl isocyanate is easily polymerized. The equivalent number of the amines is determined as the value of the number of nitrogen atoms multiplied by the mole number. (For example, 1 mol of an imidazole having two nitrogen atoms corresponds to 2 equivalent.)

The mixing treatment of adding the above described amines and epoxy compound to the hydrolyzable chlorine containing (meth)acryloyloxyalkyl isocyanate is necessary to be carried out at a temperature of from 110° C. to 160° C., preferably 120 to 150° C. The treatment time, which is not particularly limited, is properly about from 30 min to 3 hr.

The treatment is carried out using the amines and the epoxy compound at a prescribed temperature in this manner and thereby it is possible to vastly decrease the hydrolyzable chlorine contained in the (meth)acryloyloxyalkyl isocyanate. Specifically, (meth)acryloyloxyalkyl isocyanate having a hydrolyzable chlorine content of several hundred ppm is subjected to this treatment and then distillation procedure once, as described later and thereby the content thereof can be reduced to not more than 10 ppm.

When the treatment temperature is lower than 110° C., hydrolyzable chlorine cannot be sufficiently removed by reaction and the hydrolyzable chlorine content cannot be removed until not more than 10 ppm finally. When the treatment temperature is over 160° C., the yield is liable to be lowered remarkedly by polymerization.

After this mixing treatment, the high purity (meth)acryloyloxyalkyl isocyanate ((meth)acryloyloxyalkyl isocyanate composition having a decreased hydrolyzable chlorine content) is isolated. The isolation method may include distillation, crystallization, extraction, column treatment and the like, and particularly the distillation is preferred.

When the (meth)acryloyloxyalkyl isocyanate is isolated by distillation, the procedure and the apparatus used in the distillation steps are not particularly limited and further it is preferred to use an apparatus equipped with rectification and refluxing devices. Furthermore, it is also possible to use a thin film distillation apparatus. The distillation is desirably carried out at the lowest possible temperature in order to avoid unnecessary heat history, and usually carried out at a pot inside temperature of not higher than 120° C. Further, in order to prevent polymerization, oxygen diluted with an inert gas and nitrogen monoxide may be fed into the system at the distillation.

In the process of the present invention, in order to prevent the (meth)acryloyloxyalkyl isocyanate from polymerization, it is preferred to carry out the purification procedure in the presence of a polymerization inhibitor. In isolating the (meth)acryloyloxyalkyl isocyanate, because polymerization is easily caused, it is particularly preferred to carry out the distillation in the presence of the polymerization inhibitor. As the polymerization inhibitor, phenothiazine is preferably used in particular.

In the mixing treatment steps using the epoxy compound and the amines, the phenothiazine may be added once prior to the mixing treatment or during the mixing treatment, or may be separated and then added two or more times intermittently or continuously.

After the mixing treatment steps using the epoxy compound and the amines, it is preferred to further add phenothiazine and carry out the distillation. In this case, in any step of the distillation steps, it may be added, for example, it may be added once prior to the distillation or during the distillation, or it may be separated into two or more and then added intermittently or continuously. It is particularly preferred that phenothiazine is further added prior to the distillation.

The phenothiazine is added, as the total addition amount in the mixing treatment and the distillation steps, in an amount of preferably not less than 5% by mass, more preferably not less than 7% by mass, furthermore preferably not less than 10% by mass based on the raw material (meth)acryloyloxyalkyl isocyanate, i.e. (meth)acryloyloxyalkyl isocyanate containing hydrolyzable chlorine.

With regard to the upper limit of the amount of phenothiazine, it is added in a large amount as long as the treatment procedure with the epoxy compound and the amines and the distillation thereof are not hindered. From the economical viewpoint, it is added in an amount of preferably not more than 50% by mass, more preferably not more than 20% by mass. Particularly, it is preferred to add phenothiazine in an amount of from 0.1 to 20% by mass based on the raw material (meth)acryloyloxyalkyl isocyanate followed by mixing treatment, and to further add phenothiazine in an amount of from 3 to 30% by mass based on the raw material (meth)acryloyloxyalkyl isocyanate followed by distillation.

Furthermore, a polymerization inhibitor which is usually used for (meth)acrylate, for example, a phenol polymerization inhibitor or quinones such as hydroquinone and the like may be used with phenothiazine.

EXAMPLE

The present invention will be described in more detail with reference to the non-limiting following examples. The unit ppm is a value of mass/mass.

In Examples and Comparative Examples, the content of hydrolyzable chlorine was determined by introducing 35 ml of methyl alcohol, 15 ml of water and 5 g of a specimen into a 100 ml volume Erlenmeyer flask, fixing a reflux condenser to the flask and refluxing with heat for 30 min, thereafter cooling to room temperature and conducting potentiometric titration by the use of a N/100 silver nitrate solution.

Example 1

To a 2000 mL volume glass reactor equipped with a fractionating column, thermometer, stirrer and hot bath, 1400 g of methacryloyloxyethyl isocyanate having a hydrolyzable chlorine content of 150 ppm (boiling point: 211° C.), 224 g of an epoxidated oil type plasticizer having an oxirane oxygen content of 6% (molecular weight: about 500, iodine value: 6), 9.8 g of 2,6-ditertiary-butyl-4-methyl phenol, 70 g of phenothiazine and 3.78 g of 2-ethyl-4-methyl imidazole were fed and stirred at 120° C. for 2 hr. Subsequently, 91 g of phenothiazine was added to the mixture and distilled at about 0.7 kPa. The initial fraction was collected in an amount of about 10% of the fed amount. Thereafter, a receiving vessel was changed and 900 g of a purified methacryloyloxyethyl isocyanate was prepared. The purified compound had a hydrolyzable chlorine content of 8 ppm.

Example 2

To a 1000 mL volume glass reactor equipped with a fractionating column, thermometer, stirrer and hot bath, 500 g of methacryloyloxyethyl isocyanate having a hydrolyzable chlorine content of 190 ppm (boiling point: 211° C.), 80 g of an epoxidated oil type plasticizer having an oxirane oxygen content of 6% (molecular weight: about 500, iodine value: 6), 3.5 g of 2,6-ditertiary-butyl-4-methyl phenol, 25 g of phenothiazine and 1.35 g of 2-ethyl-4-methyl imidazole were fed and stirred at 120° C. for 2 hr. Subsequently, 32.5 g of phenothiazine was added and distilled at about 0.7 kPa. The initial fraction was collected in an amount of about 10% of the fed amount. Thereafter, a receiving vessel was changed and 300 g of a purified methacryloyloxyethyl isocyanate was prepared. The purified compound had a hydrolyzable chlorine content of 7 ppm.

Example 3

To a 500 mL volume glass reactor equipped with a fractionating column, thermometer, stirrer and hot bath, 200 g of methacryloyloxyethyl isocyanate having a hydrolyzable chlorine content of 150 ppm (boiling point: 211° C.), 32 g of an epoxidated oil type plasticizer having an oxirane oxygen content of 6% (molecular weight: about 500, iodine value: 6), 1.4 g of 2,6-ditertiary-butyl-4-methyl phenol, 2 g of phenothiazine and 0.45 g of 2-ethyl-4-methyl imidazole were fed and stirred at 120° C. for 2 hr. Subsequently, 13 g of phenothiazine was added and distilled at about 0.7 kPa. The initial fraction was collected in an amount of about 20% of the fed amount. Thereafter, a receiving vessel was changed and 100 g of a purified methacryloyloxyethyl isocyanate was prepared. The purified compound had a hydrolyzable chlorine content of 5 ppm.

Example 4

To a 500 mL volume glass reactor equipped with a fractionating column, thermometer, stirrer and hot bath, 200 g of methacryloyloxyethyl isocyanate having a hydrolyzable chlorine content of 150 ppm (boiling point: 211° C.), 32 g of an epoxidated oil type plasticizer having an oxirane oxygen content of 6% (molecular weight: about 500, iodine value: 6), 1.4 g of 2,6-ditertiary-butyl-4-methyl phenol, 2 g of phenothiazine and 0.3 g of triethylene tetramine were fed and stirred at 120° C. for 2 hr. Subsequently, 13 g of phenothiazine was added and distilled at about 0.7 kPa. The initial fraction was collected in an amount of about 20% of the fed amount. Thereafter, a receiving vessel was changed and 100 g of a purified methacryloyloxyethyl isocyanate was prepared. The purified compound had a hydrolyzable chlorine content of 9 ppm.

Example 5

To a 500 mL volume glass reactor equipped with a fractionating column, thermometer, stirrer and hot bath, 200 g of methacryloyloxyethyl isocyanate having a hydrolyzable chlorine content of 150 ppm (boiling point: 211° C.), 32 g of an epoxidated oil type plasticizer having an oxirane oxygen content of 6% (molecular weight: about 500, iodine value: 6), 1.4 g of 2,6-ditertiary-butyl-4-methyl phenol, 2 g of phenothiazine and 0.45 g of 2-ethyl-4-methyl imidazole were fed and stirred at 150° C. for 2 hr. Subsequently, 13 g of phenothiazine was added and distilled at about 0.7 kPa. The initial fraction was collected in an amount of about 15% of the fed amount. Thereafter, a receiving vessel was changed and 110 g of a purified methacryloyloxyethyl isocyanate was prepared. The purified compound had a hydrolyzable chlorine content of 5 ppm.

Testing Example 1

(Effect of Preventing Polymerization Using Phenothiazine)

To a 300 mL volume glass reactor equipped with a fractionating column, thermometer, stirrer and hot bath, 100 g of methacryloyloxyethyl isocyanate having a hydrolyzable chlorine content of 150 ppm (boiling point: 211° C.), 16 g of an epoxidated oil type plasticizer having an oxirane oxygen content of 6% (molecular weight: about 500, iodine value: 6), 0.7 g of 2,6-ditertiary-butyl-4-methyl phenol, A g of phenothiazine and 0.27 g of 2-ethyl-4-methyl imidazole were fed and stirred at 120° C. for 2 hr. Subsequently, B g of phenothiazine was added and distilled at about 0.7 kPa.

The above procedures each were repeated six times with changing the amounts A and B. The results are as follows.

A g=0.5 g and B g=0.5 g:

In all the 6 time procedures, when about half of the reactant was distilled, it was polymerized.

A g=2.5 g and B g=2.5 g:

Of the six time procedures, in the three time procedures, polymerization was not occurred, and in the other three time procedures, polymers were observed, however, about 80% of the reactant could be distilled.

A g=1.0 g and B g=6.5 g:

Of the six time procedures, in the five time procedures, polymerization was not occurred, and in the one time procedure, polymers were observed, however, the reactant could be distilled until the end.

A g=5.0 g and B g=6.5 g:

In the six time procedures, the increase in viscosity for inducing polymerization was not observed at all.

Comparative Example 1

To a 500 mL volume glass reactor equipped with a fractionating column, thermometer, stirrer and hot bath, 200 g of methacryloyloxyethyl isocyanate having a hydrolyzable chlorine content of 150 ppm (boiling point: 211° C.), 32 g of an epoxidated oil type plasticizer having an oxirane oxygen content of 6% (molecular weight: about 500, iodine value: 6), 1.4 g of 2,6-ditertiary-butyl-4-methyl phenol, 2 g of phenothiazine and 0.45 g of 2-ethyl-4-methyl imidazole were fed and stirred at 60° C. for 2 hr. Subsequently, 13 g of phenothiazine was added and distilled at about 0.7 kPa. The initial fraction was collected in an amount of about 20% of the fed amount. Thereafter, a receiving vessel was changed and 100 g of a purified methacryloyloxyethyl isocyanate was prepared. The purified compound had a hydrolyzable chlorine content of 25 ppm.

Comparative Example 2

To a 200 mL volume glass reactor equipped with a fractionating column, thermometer, stirrer and hot bath, 50 g of methacryloyloxyethyl isocyanate having a hydrolyzable chlorine content of 150 ppm (boiling point: 211° C.), 8 g of an epoxidated oil type plasticizer having an oxirane oxygen content of 6% (molecular weight: about 500, iodine value: 6), 0.75 g of 2,6-ditertiary-butyl-4-methyl phenol and 0.1 g of phenothiazine were fed and stirred at 120° C. for 2 hr. Subsequently, 0.1 g of phenothiazine was added and distilled at about 0.7 kPa. The initial fraction was collected in an amount of about 20% of the fed amount. Thereafter, a receiving vessel was changed and 20 g of a purified methacryloyloxyethyl isocyanate was prepared. The purified compound had a hydrolyzable chlorine content of 30 ppm.

Comparative Example 3

To a 200 mL volume glass reactor equipped with a fractionating column, thermometer, stirrer and hot bath, 50 g of methacryloyloxyethyl isocyanate having a hydrolyzable chlorine content of 150 ppm (boiling point: 211° C.), 8 g of an epoxidated oil type plasticizer having an oxirane oxygen content of 6% (molecular weight: about 500, iodine value: 6), 0.75 g of 2,6-ditertiary-butyl-4-methyl phenol and 0.1 g of phenothiazine were fed and stirred at 60° C. for 2 hr. Subsequently, 0.1 g of phenothiazine was added and distilled at about 0.7 kPa. The initial fraction was collected in an amount of about 20% of the fed amount. Thereafter, a receiving vessel was changed and 20 g of a purified methacryloyloxyethyl isocyanate was prepared. The purified compound had a hydrolyzable chlorine content of 70 ppm.

Comparative Example 4

To a 200 mL volume glass reactor equipped with a fractionating column, thermometer, stirrer and hot bath, 50 g of methacryloyloxyethyl isocyanate having a hydrolyzable chlorine content of 150 ppm (boiling point: 211° C.), 8 g of an epoxidated oil type plasticizer having an oxirane oxygen content of 6% (molecular weight: about 500, iodine value: 6), 0.35 g of 2,6-ditertiary-butyl-4-methyl phenol and 0.1 g of phenothiazine were fed and stirred at 150° C. for 2 hr. Subsequently, the distillation thereof was carried out at about 0.7 kPa. The initial fraction was collected in an amount of about 20% of the fed amount. Thereafter, a receiving vessel was changed and 20 g of a purified methacryloyloxyethyl isocyanate was prepared. The purified compound had a hydrolyzable chlorine content of 25 ppm.

The invention claimed is:

1. A process for preparing a (meth)acryloyloxyalkyl isocyanate which process comprises:

subjecting a hydrolyzable chlorine containing (meth)acryloyloxyalkyl isocyanate to mixing treatment with an epoxy compound and at least one of an amine and an imidazole at a temperature of from 110 to 160° C. to prepare a mixture; and preparing a (meth)acryloyloxyalkyl isocyanate from the resulting mixture wherein the mixing treatment is carried out by adding a polymenrization inhibitor.

2. The process for preparing a (meth)acryloyloxyalkyl isocyanate according to claim 1 which process further comprises distilling the resulting mixture to isolate a (meth)acryloyloxyalkyl isocyanate, after the mixing treatment.

3. The process for preparing a (meth)acryloyloxyalkyl isocyanate according to claim 1 which process further comprises carrying out distillation with adding a polymerization inhibitor after the mixing treatment.

4. The process for preparing a (meth)acryloyloxyalkyl isocyanate according to claim 1 wherein the polymerization inhibitor is phenothiazine.

5. The process for preparing a (meth)acryloyloxyalkyl isocyanate according to claim 4 wherein the mixing treatment is carried out with adding phenothiazine in an amount of from 0.1 to 20% by mass based on the raw material (meth)acryloyloxyalkyl isocyanate and then the distillation is carried out with adding phenothiazine in an amount of from 3 to 30% by mass based on the raw material (meth)acryloyloxyalkyl isocyanate.

6. The process for preparing a (meth)acryloyloxyalkyl isocyanate according to claim 4 wherein the total amount of phenothiazine added is from 5 to 50% by mass based on the raw material (meth)acryloyloxyalkyl isocyanate.

7. The process for preparing a (meth)acryloyloxyalkyl isocyanate according to claim 2 wherein the distillation is carried out at a temperature of not higher than 120° C.

8. The process for preparing a (meth)acryloyloxyalkyl isocyanate according to claim 1 or 2 wherein the at least one of an amine and an imidazole is at least one selected from 2-alkyl-4-alkyl imidazole (provided that each alkyl group independently has a carbon number of 1 to 3), trialkyl amine (provided that each alkyl group independently has a carbon number of 4 to 15) and a compound represented by the following formula [A]:

$$H_2N-(CH_2CH_2NH)_n-H \quad [A]$$

wherein n is an integer of 2 or more.

9. The process for preparing a (meth)acryloyloxyalkyl isocyanate according to claim 8 wherein the at least one of an amine and an imidazole is 2-ethyl-4-methylimidazole.

10. The process for preparing a (meth)acryloyloxyalkyl isocyanate according to claim 1 or 2 wherein the (meth)acryloyloxyalkyl isocyanate is (meth)acryoyloxyethyl isocyanate.

* * * * *